United States Patent [19]

Maier

[11] 4,387,941
[45] Jun. 14, 1983

[54] WORK PLACE ARRANGEMENT

[75] Inventor: Klaus Maier, Heidenheim, Fed. Rep. of Germany

[73] Assignee: Strohm & Maier Labormobel GmbH, Heidenheim, Fed. Rep. of Germany

[21] Appl. No.: 196,151

[22] Filed: Oct. 10, 1980

[30] Foreign Application Priority Data

Nov. 6, 1979 [DE] Fed. Rep. of Germany ....... 2944671

[51] Int. Cl.³ ............................................. A47B 77/08
[52] U.S. Cl. .................................. 312/194; 312/196; 312/209; 312/223; 433/77
[58] Field of Search ............... 312/209, 194, 195, 196, 312/236, 223; 433/77, 79

[56] References Cited

U.S. PATENT DOCUMENTS

| | | | |
|---|---|---|---|
| D. 186,881 | 12/1959 | Ogg | 312/209 |
| 478,830 | 7/1892 | Wenman | 312/209 |
| 2,863,708 | 12/1958 | Cahn | 312/236 |
| 3,226,733 | 1/1966 | Ashton | 433/77 |
| 3,437,390 | 4/1969 | Evans | 312/196 |
| 3,524,256 | 8/1970 | Barker | 312/209 |
| 3,530,513 | 9/1970 | Maurer et al. | 312/209 |
| 3,553,840 | 1/1971 | Bordelon | 433/77 |
| 3,784,270 | 1/1974 | DeLapp | 312/209 |
| 4,112,916 | 9/1978 | Guibert | 312/236 |
| 4,138,815 | 2/1979 | Williams et al. | 433/77 |

FOREIGN PATENT DOCUMENTS

| | | | |
|---|---|---|---|
| 195569 | 2/1958 | Austria | 433/77 |
| 1236145 | 3/1967 | Fed. Rep. of Germany | 312/209 |
| 2253495 | 8/1975 | France | 433/77 |

Primary Examiner—Victor N. Sakran
Attorney, Agent, or Firm—Strimbeck, Davis & Soloway

[57] ABSTRACT

A work place arrangement particularly adapted for laboratory work is described. The work place arrangement comprises a workbench including at least one attached board, at least one drawer, at least one arm rest, at least one working instrument or work tool and supply lines for the working instrument or tool, in which:

(a) the attached board is adapted to receive the working instruments or tools located in or on the attached board, and the supply lines for the working instruments or tools housed in the attached board, (b) the arm rests comprise a left half and a right half formed as a joint unit firmly affixed on the front side of the bench at ergonomic height below the bench top main work surface; and (c) including a suction device having a suction opening located in the arm-rests unit centrally thereof between the left and right halves of said arm-rests. In a preferred embodiment of the invention two or more work benches are joined to form a working landscape.

8 Claims, 4 Drawing Figures

WORK PLACE ARRANGEMENT

The present invention relates to a work place arrangement, and more particularly to a workbench including one or more attached boards on the workbench, drawers, one or more arm rests and one or more instruments such as grinders, air-blow-off-nozzles, meters, plug boxes, suction devices and the like. The invention has particular utility in connection with a work place for a dental laboratory, and will be described in connection with such utility.

In dental laboratories are performed numerous different working procedures requiring different working instruments and means.

In known laboratory work place arrangements there are provided at different sites diverse storage surfaces and attached boards. The same applies to the required working instruments, some of which typically are fixedly mounted upon the workbench, and others of which may lay with their feed lines loose upon the workbench. To facilitate operations such as grinding or milling, swivel arm rests may also be disposed on the bench. However, such known work places are designed without regard for balance. Thus, numerous manual motions are needed for separate working procedures, leading to worker fatigue.

It is thus a primary object of the present invention to provide a work place arrangement which overcomes the aforesaid problems of the prior art. A more specific object of the present invention is to provide a dental laboratory work place arrangement designed with ergonomic standards in mind, and in which it is possible to work comfortably and expediently.

In accordance with the present invention there is provided a work place arrangement comprising a workbench including at least one attached board, at least one drawer, at least one arm rest and at least one working instrument or work tool, and wherein:
  (a) said attached board is adapted to receive said working instruments located in or on the attached board, and supply lines for the working instruments or tools housed in the attached board,
  (b) including two arm rests comprised of a left half and a right half formed as a joint unit which is firmly affixed on the front side of the workbench at ergonomic height beneath the bench top main work surface, and
  (c) including a suction device having a suction opening located in the arm-rests unit centrally thereof between the left and right halves of the arm rests unit.

The foregoing work place arrangement provides a number of advantages over prior art arrangements. For one, by locating the working instruments in or on the attached board, they lie centrally within easy grasp. In addition, the work place is free of interfering supply lines, since the supply lines are housed in the working board. A particular feature and advantage of the present invention is the provision of the fixed arm-rests unit at the front side of the work bench at a height beneath the bench top main work surface with a suction opening between the left and right halves of the arm rests unit. By virtue of this feature a worker can very comfortably carry out grinding or milling operations since his arms are equally supported during this work. And the worker does not have to make provision for removing grinding dust since the dust will be directly sucked away by the suction opening disposed between the two arm rest halves.

In one embodiment of the present invention a push-button is disposed on the top of the arm-rests unit for controlling the suction device. A particular advantage of this embodiment is that it puts the push-button for controlling the suction device within reach of a worker's elbow, whereby a worker can, in a simple manner, control the suction device with his elbow, while leaving both hands free for the workpiece and tool.

In another embodiment of the invention a metal plate is provided in the arm-rests unit adjacent the suction opening. The metal plate serves as heat protection for the arm rests unit.

In still another embodiment of the invention a trash bin with several compartments is located beneath the armrests unit, e.g., for receiving a plaster cast, tools and dirt particles. Preferably the drawer is removeable.

In still another embodiment of the invention the top of the attached board is forwardly inclined relative to the front side of the bench. Forwardly inclining the board gives a worker better sight of the workpieces, tools, work trays and the like. Also, if desired, the top of the attached board may be furnished with a depression for accommodating the handle of the grinder or cutter, whereby freeing the workbench top main work surface.

In a particularly preferred embodiment of the invention the work place arrangement includes an equilateral triangular plate, the sides of which are equal in length to the width of the workbench, whereby two or three workbenches may be joined at the triangular plate to form a unit. As will become clear from the description following the triangular plate makes it possible to combine a plurality of laboratory workbenches with each other in any various configurations, whereby to provide desired working landscapes. It is thus possible to construct work bench groups, for example, particularly adapted for working ceramics, precious metals, plastics or steel. Preferably common supply lines for such workbench groups will be housed in the triangular plates. Furthermore, if desired, the triangular plates may themselves include storage depressions and/or storage boards. Also, if desired, for work bench groups designed for ceramic working, a rotatably mounted ceramic oven may be provided on the triangular plate between two or three benches.

Other features and advantages of the present invention will become apparent from the following detailed description taken in connection with the accompanying drawings wherein like numerals denote like elements, and wherein.

Figure 1:
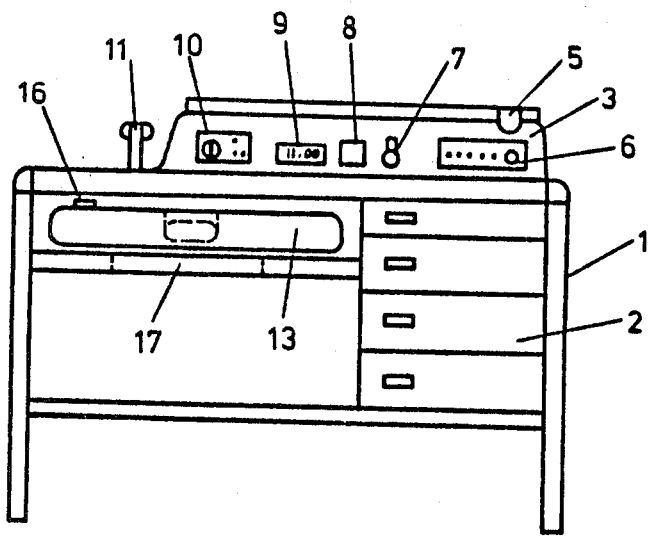
FIG. 1 is a front plan view of a laboratory work place according to the present invention.
Figure 2:
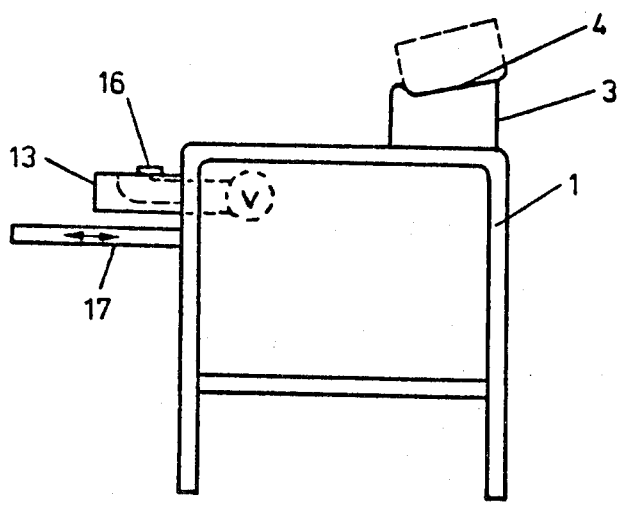
FIG. 2 is a side view of the laboratory work place of FIG. 1.
Figure 3:
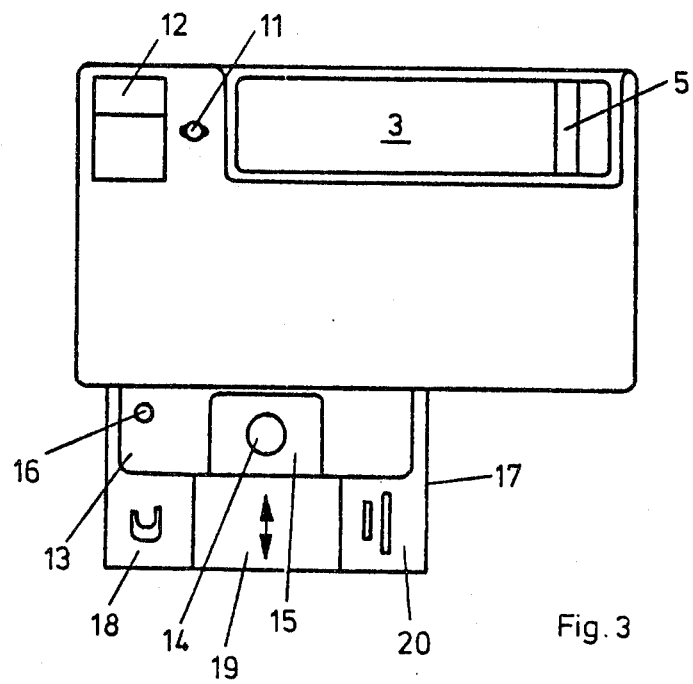
FIG. 3 is a top plan view of the laboratory work place of FIG. 1.

Referring to FIGS. 1 to 3 of the drawings there is shown a work place which comprises a workbench preferably formed of a plastic material, and having a metal frame, e.g. aluminum for ensuring required stability. On the front right hand side of the workbench 1 are disposed several drawers 2. On the bench top plate, somewhat shifted to the right, there is an attached board 3 having a top side 4 forwardly inclined and built as a storage surface. Workpieces, tools and working trays can be stored on the top side 4 (as indicated by dotted lines). In addition board 3 is provided with a depression 5 which is adapted to accommodate the handle of a working tool such as a milling or grinding tool 6. In board 3 there is also mounted a removable air-blow-off-nozzle 7, a plug box 8, a clock 9 and an electric wax meter 10. The supply lines for these various working tools and instruments are housed in board 3. Next to board 3 is arranged a gas connection 11. Housing the various working tools and instruments in board 3 is obviously optional. Individual working tools and instruments likewise can be eliminated.

Adjacent to gas connection 11 (which likewise is optional), there is molded in the top of the workbench an instrument tray 12.

At ergonomic height beneath the workbench work top main work surface is the counter portion 13. The latter comprises a left arm rest half and a right arm rest half formed as a joint unit which is firmly fixed to the front of the workbench. In the central zone of the counter portion 13, i.e. between the left and right halves, adjacent the counter portion connection to the workbench, there is provided a suction opening 14 of a suction device. As protection against heat, suction opening 14 preferably is surrounded by a metal plate 15. On the counter portion 13 there is provided to one side, e.g., to the left, a push-button 16 for controlling the suction device. Preferably push-button 16 is located so as to be within elbow reach of a worker when he assumes normal working position at the workbench.

Beneath the counter portion 13 is disposed a trash bin 17 which preferably includes a plurality of compartments, e.g., three compartments, 18, 19 and 20. Central compartment 19 may serve for receiving dirt particles, while plaster casts and tools can be stored in the two outer compartments 18 and 20.

Figure 4:
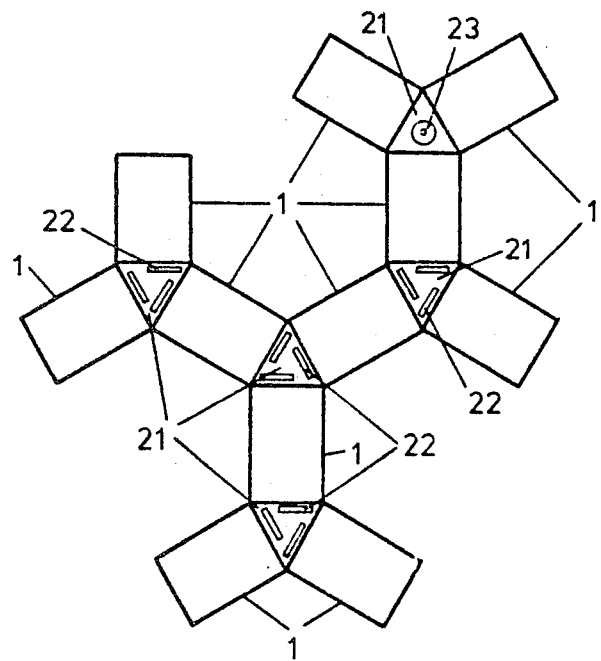
FIG. 4 shows an arrangement of several laboratory work places in a group according to the present invention.

FIG. 4 shows how several laboratory workbenches 1 made in accordance with the present invention may be advantageously combined to form a working landscape. This is made possible by the provision of a triangular plate 21 the sides of which correspond in length to the width of the workbenches. With this arrangement it is possible to join three workbenches radially with each other. If desired, triangular plates 21 also may be provided with storage trays 22; and, as noted supra, in the case of workbench groups designed for ceramic work, a rotatably mounted ceramic oven 23 may be provided on triangular plate 21.

The supply lines for the two or three workbenches, respectively, preferably are conveniently housed under triangular plates 21. If desired, triangular plates 21 optionally can be built as closed triangular blocks.

Various modifications and variations will be obvious to one skilled in the art, and may be made in the foregoing invention without departing from the spirit and scope of the invention. Accordingly, it is intended that all matter contained in the above description or shown in the accompanying drawings shall be interpreted in an illustrative and not in a limiting sense.

What is claimed is:

1. In a work place arrangement which comprises a workbench including at least one attached board, at least one drawer, at least one arm rest, at least one working instrument or tool, and supply lines for said working instruments or tools, the improvement wherein:
   (a) said attached board is adapted to receive said working instruments or tools and to incorporate supply lines for said working instruments or tools, so received
   (b) said arm rests comprise a left half and a right half which together form a counter portion firmly affixed on the front side of said bench at ergonomic height below the bench top main work surface, and including
   (c) a suction device having a suction opening located in said arm-rests unit, centrally thereof, between said left and right arm rest halves of said counter portion and a push-button control located on the top side of said counter portion for actuating said suction device,
   (d) a metal plate on said counter portion adjacent said suction opening, and
   (e) a trash bin disposed beneath said counter portion,
   (f) wherein the top side of said attached board is forwardly inclined relative to said workbench front side
   (g) wherein the top side surface of said attached board has a depression for accommodating the handle of a work tool.

2. A work place landscape comprising at least two workbenches according to any one of claim 1, and including an equilateral triangular plate, the sides of which correspond in length to the width of said workbenches, and wherein said workbenches are joined at their sides to said triangular plate to form a unit.

3. In a work place landscape according to claim 2, wherein common supply lines for said unit are housed within said triangular plate.

4. In a work place landscape according to claim 2, and including storage depressions formed in said triangular plate.

5. In a work place landscape according to claim 2, and including storage boards located on said triangular plate.

6. In a work place landscape according to claim 2, and further comprising a rotatable ceramic oven on said triangular plate.

7. In a work place landscape according to claim 2, and comprising two said workbenches.

8. In a work place landscape according to claim 2, and comprising three said workbenches.

* * * * *